(12) United States Patent
Fu et al.

(10) Patent No.: US 6,864,057 B2
(45) Date of Patent: Mar. 8, 2005

(54) CONSTRUCTION OF UNI-DIRECTIONALLY CLONED CDNA LIBRARIES FROM MESSENGER RNA FOR IMPROVED 3' END DNA SEQUENCING

(75) Inventors: Glenn K. Fu, El Cerrito, CA (US); Steven Starnes, East Palo Alto, CA (US); Laura L. Stuve, Los Gatos, CA (US)

(73) Assignee: Incyte Corporation, Palo Alto, CA (US)

( * ) Notice: Subject to any disclaimer, the term of this patent is extended or adjusted under 35 U.S.C. 154(b) by 264 days.

(21) Appl. No.: 10/039,890

(22) Filed: Jan. 4, 2002

(65) Prior Publication Data

US 2002/0142331 A1 Oct. 3, 2002

Related U.S. Application Data

(62) Division of application No. 09/549,770, filed on Apr. 14, 2000, now Pat. No. 6,387,624.

(51) Int. Cl.[7] ........................... C12Q 1/68; C12P 19/34; C07H 21/02; C07H 21/04
(52) U.S. Cl. ....................... 435/6; 435/91.51; 536/23.1; 536/24.3
(58) Field of Search ................. 435/6, 91.51; 536/23.1, 536/24.3

(56) References Cited

U.S. PATENT DOCUMENTS

| | | | |
|---|---|---|---|
| 5,104,792 A | | 4/1992 | Silver et al. |
| 5,262,311 A | | 11/1993 | Pardee et al. |
| 5,580,726 A | * | 12/1996 | Villeponteau et al. |
| 5,665,547 A | | 9/1997 | Pardee et al. |
| 5,712,126 A | * | 1/1998 | Weissman et al. |
| 5,759,820 A | * | 6/1998 | Hornes et al. |
| 5,837,468 A | | 11/1998 | Wang et al. |
| 5,853,991 A | * | 12/1998 | Wang et al. |
| 5,965,409 A | | 10/1999 | Pardee et al. |
| 5,994,058 A | | 11/1999 | Senapathy |
| 6,022,715 A | * | 2/2000 | Merenkova et al. |
| 6,153,740 A | * | 11/2000 | Young et al. |
| 6,316,197 B1 | * | 11/2001 | Das et al. |
| 6,387,624 B1 | * | 5/2002 | Fu et al. |
| 6,436,676 B1 | * | 8/2002 | Guegler et al. |
| 6,509,175 B2 | * | 1/2003 | Fu et al. |
| 6,548,633 B1 | * | 4/2003 | Edwards et al. |

FOREIGN PATENT DOCUMENTS

| | | |
|---|---|---|
| WO | WO 93/18176 | 9/1993 |
| WO | WO 94/26928 | 11/1994 |
| WO | WO 98/51789 | 11/1998 |
| WO | WO 00/00646 | 1/2000 |
| WO | WO 95/13369 | 1/2000 |
| WO | WO 00/56936 | 9/2000 |

OTHER PUBLICATIONS

Fislage et al., "*Primer Design for a Prokaryotic Differential Display RT–PCR*", Nucleic Acid Research vol. 25(9): 1830–1835.

Henikoff S., "*Unidirectional Digestion with Exonuclease III in SNA Sequence Analysis*", Methods in Enzymology 155: 156–165 (1987).

Hwang et al., "*Single Pass Sequencing of a Unidirectional Human fetal Heart cDNA Library to Discover Novel Genes of the Cardiovascular System*", J. of Molecular and Cellular Cardiology 26: 1329–1333 (1994).

Khan et al., "*Efficient Double Stranded Sequencing of cDNA Clones Containing Long Poly(A) Tails Using Anchored Poly(dt) Primers*", Nucleic Acid Research, vol. 19(7): 1715 (1990).

Moore et al., "*Design of PCR Primers that Detect only mRNA in the Presence of DNA*", Nucleic Acid Research, vol. 18(7): 1921 (1990).

Peterson et al., "*An Improved Method for Construction if Directionally Cloned cDNA Libraries From Microdissected Cells*", Cancer Research 58: 5326–5328 (Dec. 1, 1998).

Thweatt et al., "*A Universal Primer Mixture for Sequence Determination at the 3' Ends of cDNAs*", Analytical Biochemistry 190: 314–316 (1990).

Wang, et al., "*Screening poly(da/dt)–cDNAs for gene identification*", PNAs 97(8): 4162–4167 (Apr. 11, 2000).

* cited by examiner

Primary Examiner—Ethan Whisenant
(74) Attorney, Agent, or Firm—Incyte Corporation

(57) ABSTRACT

Methods are provide for preparing cDNA corresponding to a mRNA. In the subject methods, a mRNA is first contacted with a mixture of primers under first strand cDNA synthesis conditions. The primer mixture contains primers that have at least 10 contiguous deoxythymidines, a double stranded restriction enzyme recognition sequence near one end and a non-polyA-complementary region near the other end, where the non-polyA-complementary region is -VV, -VTV, -VTTV, -VTTTV, and -VVVVV. The resultant cDNA is modified such that the polyT tail is substantially removed. The modified cDNA is then ligated into a vector. The subject methods find use in a variety of applications, and find particular use in the sequencing of DNA and in the synthesis of cDNA libraries.

12 Claims, 1 Drawing Sheet

FIGURE 1.

| | |
|---|---|
| 5'pGACTAGTTCTAGATCGCGACTGGATTTTTTTTTTTTTTTTTTTTVV | Seq ID. No. 11 |
| 5'pGACTAGTTCTAGATCGCGACTGGATTTTTTTTTTTTTTTTTTTVTV | Seq ID. No. 12 |
| 5'pGACTAGTTCTAGATCGCGACTGGATTTTTTTTTTTTTTTTTTVTTV | Seq ID. No. 13 |
| 5'pGACTAGTTCTAGATCGCGACTGGATTTTTTTTTTTTTTTTTVTTTV | Seq ID. No. 14 |
| 5'pGACTAGTTCTAGATCGCGACTGGATTTTTTTTTTTTTTTTTVVVVV | Seq ID. No. 15 |

SEQUENCE LISTING

<160> NUMBER OF SEQ ID NOS: 15

<210> SEQ ID NO 1
<211> LENGTH: 6
<212> TYPE: DNA
<213> ORGANISM: Homo sapiens
<220> FEATURE:
<221> NAME/KEY: misc_feature
<222> LOCATION: (1)...(6)
<223> OTHER INFORMATION: v = A, C or G

<400> SEQUENCE: 1 tttttv                                                                      6

<210> SEQ ID NO 2
<211> LENGTH: 7
<212> TYPE: DNA
<213> ORGANISM: Homo sapiens
<220> FEATURE:
<221> NAME/KEY: misc_feature
<222> LOCATION: (1)...(7)
<223> OTHER INFORMATION: v = A,C or G

<400> SEQUENCE: 2 tttttvv                                                                     7

<210> SEQ ID NO 3
<211> LENGTH: 8
<212> TYPE: DNA
<213> ORGANISM: Homo sapiens
<220> FEATURE:
<221> NAME/KEY: misc_feature
<222> LOCATION: (1)...(8)
<223> OTHER INFORMATION: v = A, C or G

<400> SEQUENCE: 3 tttttvtv                                                                    8

<210> SEQ ID NO 4
<211> LENGTH: 9
<212> TYPE: DNA
<213> ORGANISM: Homo sapiens
<220> FEATURE:
<221> NAME/KEY: misc_feature
<222> LOCATION: (1)...(9)
<223> OTHER INFORMATION: v = A, C or G

<400> SEQUENCE: 4 tttttvttv                                                                   9

<210> SEQ ID NO 5
<211> LENGTH: 10
<212> TYPE: DNA
<213> ORGANISM: Homo sapiens
<220> FEATURE:
<221> NAME/KEY: misc_feature
<222> LOCATION: (1)...(10)
<223> OTHER INFORMATION: v = A, C or G

<400> SEQUENCE: 5 tttttvtttv                                                                  10

<210> SEQ ID NO 6
<211> LENGTH: 8
<212> TYPE: DNA
<213> ORGANISM: Homo sapiens

```
<220> FEATURE:
<221> NAME/KEY: misc_feature
<222> LOCATION: (1)...(8)
<223> OTHER INFORMATION: v = A, C or G

<400> SEQUENCE: 6 tttttvvv                                                                        8

<210> SEQ ID NO 7
<211> LENGTH: 9
<212> TYPE: DNA
<213> ORGANISM: Homo sapiens
<220> FEATURE:
<221> NAME/KEY: misc_feature
<222> LOCATION: (1)...(9)
<223> OTHER INFORMATION: v = A, C or G

<400> SEQUENCE: 7 tttttvtvv                                                                       9

<210> SEQ ID NO 8
<211> LENGTH: 9
<212> TYPE: DNA
<213> ORGANISM: Homo sapiens
<220> FEATURE:
<221> NAME/KEY: misc_feature
<222> LOCATION: (1)...(9)
<223> OTHER INFORMATION: v = A, C or G

<400> SEQUENCE: 8 tttttvvtv                                                                       9

<210> SEQ ID NO 9
<211> LENGTH: 10
<212> TYPE: DNA
<213> ORGANISM: Homo sapiens
<220> FEATURE:
<221> NAME/KEY: misc_feature
<222> LOCATION: (1)...(10)
<223> OTHER INFORMATION: v = A, C or G

<400> SEQUENCE: 9 tttttvtvtv                                                                     10

<210> SEQ ID NO 10
<211> LENGTH: 10
<212> TYPE: DNA
<213> ORGANISM: Homo sapiens
<220> FEATURE:
<221> NAME/KEY: misc_feature
<222> LOCATION: (1)...(10)
<223> OTHER INFORMATION: v = A, C or G

<400> SEQUENCE: 10 tttttvvvv                                                                      10

<210> SEQ ID NO 11
<211> LENGTH: 45
<212> TYPE: DNA
<213> ORGANISM: Homo sapiens
<220> FEATURE:
<221> NAME/KEY: misc_feature
<222> LOCATION: (1)...(45)
<223> OTHER INFORMATION: v = A, C or G

<400> SEQUENCE: 11
gactagttct agatcgcgac tggattttttt tttttttttt tttvv                              45
```

```
<210> SEQ ID NO 12
<211> LENGTH: 46
<212> TYPE: DNA
<213> ORGANISM: Homo sapiens
<220> FEATURE:
<221> NAME/KEY: misc_feature
<222> LOCATION: (1)...(46)
<223> OTHER INFORMATION: v = A, C or G

<400> SEQUENCE: 12
gactagttct agatcgcgac tggattttt tttttttttt tttvtv                    46

<210> SEQ ID NO 13
<211> LENGTH: 47
<212> TYPE: DNA
<213> ORGANISM: Homo sapiens
<220> FEATURE:
<221> NAME/KEY: misc_feature
<222> LOCATION: (1)...(47)
<223> OTHER INFORMATION: v = A, C or G

<400> SEQUENCE: 13
gactagttct agatcgcgac tggattttt tttttttttt tttvttv                   47

<210> SEQ ID NO 14
<211> LENGTH: 48
<212> TYPE: DNA
<213> ORGANISM: Homo sapiens
<220> FEATURE:
<221> NAME/KEY: misc_feature
<222> LOCATION: (1)...(48)
<223> OTHER INFORMATION: v = A, C or G

<400> SEQUENCE: 14
gactagttct agatcgcgac tggattttt tttttttttt tttvtttv                  48

<210> SEQ ID NO 15
<211> LENGTH: 48
<212> TYPE: DNA
<213> ORGANISM: Homo sapiens
<220> FEATURE:
<221> NAME/KEY: misc_feature
<222> LOCATION: (1)...(48)
<223> OTHER INFORMATION: v = A, C or G

<400> SEQUENCE: 15
gactagttct agatcgcgac tggattttt tttttttttt tttvvvvv                  48
```

CONSTRUCTION OF UNI-DIRECTIONALLY CLONED CDNA LIBRARIES FROM MESSENGER RNA FOR IMPROVED 3' END DNA SEQUENCING

CROSS-REFERENCE TO RELATED APPLICATIONS

This application is a divisional of prior U.S. patent application Ser. No. 09/549,770, filed Apr. 14, 2000, now U.S. Pat. No. 6,387,624.

FIELD OF INVENTION

The present invention relates generally to the field of amplifying nucleic acids, more particularly to methods for producing cDNA from mRNA, sequencing DNA, and constructing cDNA libraries.

BACKGROUND OF THE INVENTION

The characterization of cell specific gene expression finds application in a variety of disciplines, such as in the analysis of differential expression between different tissue types, different stages of cellular growth or between normal and diseased states, and the like. Fundamental to the characterization of cell specific gene expression is the detection of mRNA, and the construction of comprehensive cDNA libraries. However, the detection of mRNA is often complicated by one or more of the following factors: cell heterogeneity, paucity of material, or limits of low abundance mRNA detection.

In a general method of constructing cDNA libraries, polyA mRNA is prepared from the desired cells and the first strand of the cDNA is prepared from the polyA mRNA using a RNA-dependent DNA polymerase ("reverse transcriptase") and an oligodeoxynucleotide primer of 12 to 18 thymidine residues. In another method, the primer contains one or two nucleotides at one end that can hybridize to the mRNA sequence upstream of the polyA tail. Usually, the first polyA-non-complementary nucleotide is a deoxyadenylate, deoxyguanylate, or deoxycytidylate ("dC"), and the second nucleotide can be any deoxynucleotide. The use of 2 nucleotides can provide a more accurate positioning of the primer at the junction between mRNA and the polyA tail.

The second strand of the cDNA is synthesized by one of several methods, the more efficient of which are commonly known as "replacement synthesis" and "primed synthesis." Replacement synthesis involves the use of ribonuclease H ("RNAase H"), which cleaves the phosphodiester backbone of RNA that is in a RNA:DNA hybrid leaving a 3' hydroxyl and a 5' phosphate, to produce nicks and gaps in the mRNA strand, creating a series of RNA primers that are used by *E. coli* DNA polymerase I, or its "Klenow" fragment, to synthesize the second strand of the cDNA. This reaction is very efficient; however, the cDNAs produced most often lack the 5' terminus of the mRNA sequence.

Primed synthesis to generate the second cDNA strand is a general name for several methods which are more difficult than replacement synthesis yet clone the 5' terminal sequences with high efficiency. In general, after the synthesis of the first cDNA strand, the 3' end of the cDNA strand is extended with terminal transferase, an enzyme which adds a homopolymeric "tail" of deoxynucleotides, most commonly deoxycytidylate. This tail is then hybridized to a primer of oligodeoxyguanidylate or a synthetic fragment of DNA with an deoxyguanidylate tail and the second strand of the cDNA is synthesized using a DNA-dependent DNA polymerase.

Once both cDNA strands have been synthesized, the cDNA library is constructed by cloning the cDNAs into an appropriate plasmid or viral vector. In practice this can be done by directly ligating the blunt ends of the cDNAs into a vector which has been digested by a restriction endonuclease to produce blunt ends. Blunt end ligations are very inefficient, however, and this is not a common method of choice. A generally used method involves adding synthetic linkers or adapters containing restriction endonuclease recognition sequences to the ends of the cDNAs. The cDNAs can then be cloned into the desired vector at a greater efficiency.

One potential problem with the current method of constructing cDNA libraries is that the hybridization of the oligo dT primer to the polyA tail of the mRNA in the initial step is not perfect. The primer does not necessarily accurately position at the junction between the mRNA and its polyA tail. Therefore, there may be continuous stretches of T's in addition to the T's on the first strand primer. While this does not usually affect efficiencies in sequencing from the 5' end, it severly compromises the ability to obtain accurate and successful sequencing from the 3' (polyA tail) end. Thus, there exists a need for methods and procedures of cDNA synthesis and cloning.

SUMMARY OF THE INVENTION

Methods are provided for obtaining a DNA complementary to a mRNA by contacting the mRNA having a polyadenosine (polyA) tail with a primer mixture, where each primer in the mixture comprises at least 5 contiguous deoxythymidines and at least 2 independently selected non-deoxythymidine nucleotides near one end, and reverse transcribing the mRNA using a reverse transcriptase to produce a DNA strand complementary to the mRNA.

Methods are also provided for obtaining a DNA complementary to a mRNA by contacting the mRNA having a polyA tail with a primer mixture, where each primer in the mixture comprises at least 10 contiguous deoxythymidines and a non-polyA-complementary region near one end, and reverse transcribing the mRNA using a reverse transcriptase to produce a DNA strand complementary to the mRNA. The non-polyA-complementary region is selected from the group consisting of 3'-VV, 3'-VTV, 3'-VTVV, 3'-VTVVV, 3'-VTVVTV, 3'-VTTV, 3'-VTTTV, 3'-VVTVVV, and 3'-VVVVV, and combinations thereof, wherein V is deoxyadenosine, deoxycytidine, or deoxyguanosine, and the primer mixture may contain primers that are sense, antisense, or double stranded, and may contain a double stranded restriction enzyme sequence near the end opposite to the one containing the non-deoxythymidine nucleotides.

Methods are also provided for producing uni-directionally cloned complimentary DNA libraries from mRNA by contacting the mRNA having polyadenylated tails with a primer mixture, wherein each primer in the mixture has at least 10 contiguous deoxythymidines and at least two non-deoxythymidine nucleotides near one end and a double stranded restriction enzyme sequence at the opposite end, reverse transcribing the mRNA using a reverse transcriptase to produce a DNA strand complementary to the mRNA, modifying the complementary DNA strand wherein the polyT tail is substantially removed, and amplifying the modified cDNA strand by inserting the strand into a cloning vector uni-directionally, and amplifying using a DNA polymerase.

Methods are also provided for producing uni-directionally cloned complimentary DNA libraries from mRNA by contacting the mRNA having a polyA tail with a primer mixture wherein each primer in the mixture has at least 15 contiguous deoxythymidines having a restriction enzyme site at one end and a non-polyA-complementary region near the opposite end, wherein the non-polyA-complementary region is selected from the group consisting of 3'-VV, 3'-VTV, 3'-VTVV, 3'-VTVVV, 3'-VTVVTV, 3'-VTTV, 3'-VTTTV, 3'-VVTVVV, and 3'-VVVVV, and combinations thereof, wherein V is deoxyadenosine, deoxycytidine, or deoxyguanosine, reverse transcribing the mRNA using a reverse transcriptase to produce a cDNA strand having a polyT tail, modifying the cDNA strand wherein the polyT tail is substantially removed, and amplifying the modified cDNA strand by inserting the strand into cloning vector uni-directionally, and amplifying using a DNA polymerase. The primer mixture may contain primers that are sense, anti-sense, or double stranded, and may contain a restriction enzyme site near the end opposite to the one containing the non-deoxythymidine nucleotides.

These and other objections, advantages, and features of the invention will become apparent to those persons skilled in the art upon reading the details of the invention as more fully described below.

BRIEF DESCRIPTION OF THE DRAWINGS

FIG. 1 provides a schematic representation the mixture of primers.

DETAILED DESCRIPTION

Before the present methods and kits are described, it is to be understood that this invention is not limited to particular methods and kits described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

Definitions

It must be noted that, as used in the specification and the appended claims, the singular forms "a," "an" and "the" include plural referents unless the context clearly dictates otherwise. Thus, for example, reference to "a primer" means that more than one such primer can be present in the composition.

The term "primers" are short nucleic acids, whether occurring naturally as in a purified restriction digest or produced synthetically, usually DNA oligonucleotides, which may be annealed to a target polynucleotide by complementary base-pairing. The primer may then be extended along the target DNA strand by a DNA polymerase enzyme. Primer pairs can be used for amplification (and identification) of a nucleic acid sequence, e.g., by the polymerase chain reaction (PCR).

The term "substantially pure" means an object species is the predominant species present (i.e., on a molar basis it is more abundant than any other individual macromolecular species in the composition), and preferably a substantially purified fraction is a composition wherein the object species comprises at least about 50 percent (on a molar basis) of all macromolecular species-present. Generally, a substantially pure composition will comprise more than about 80 to 90 percent of all macromolecular species present in the composition.

The terms "complementary" and "complementarity" refer to the natural binding of polynucleotides by hydrogen bond base pairing. For example, the sequence "5' A-G-T 3'" with the complementary sequence "3' T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions Methods for PCR amplification are described in the art (PCR Technology: Principles and Applications for DNA Amplification ed. H A Erlich, Stockton Press, New York, N.Y. (1989); PCR Protocols: A Guide to Methods and Applications, eds. Innis, Gelfland, Snisky, and White, Academic Press, San Diego, Calif. (1990); Mattila et al. (1991) Nucleic Acids Res. 19: 4967; Eckert, K. A. and Kunkel, T. A. (1991) PCR Methods and Applications 1: 17 each of which are incorporated herein by reference).

In one embodiment, cDNA corresponding to mRNA is synthesized by first contacting the mRNA having a polyA tail with a mixture of primers. The primer mixture contains primers that have at least 10 contiguous deoxythymidines, a restriction enzyme site near one end and a non-polyA-complementary region near the other end, where the non-polyA-complementary region is -VV, -VTV, -VTTV, -VTTTV, and -VVVVV. The resultant cDNA is modified such that the polyT tail is substantially removed, and subsequently ligated into a vector for the synthesis of cDNA libraries.

Primers as used in the present invention typically comprise at least 5 contiguous nucleotides of a known sequence. In order to enhance specificity, longer probes and primers may also be employed, such as probes and primers that comprise at least 10, 13, 15, 17, 19, 20, 25, 30, 40, 50, 60, 70, 80, 90, 100, or at least 150 nucleotides. Probes and primers may be considerably longer than these examples, and it is understood that any length may be used.

In one embodiment of the invention, the mixture of primers contains a first primer that has at least 5 nucleotides capable of hybridizing to the polyA tail and at least one nucleotide near one end, preferably the 3'-end, that can hybridize to an mRNA sequence that is immediately upstream of the polyA tail, and contains, and at least a second primer that has at least 5 nucleotides capable of hybridizing to the polyA tail and at least two nucleotide near one end, preferably the 3'-end, that can hybridize to an mRNA sequence that is immediately upstream of the polyA tail. Thus, the mixture may contain primers having the sequences 5'-TTTTTV (Seq. ID. No. 1), 5'-TTTTTVV (Seq. ID. No. 2), 5'-TTTTTVTV (Seq. ID. No. 3), 5'-TTTTTVTTV (Seq. ID. No. 4), 5'-TTTTTVTTTV (Seq. ID. No. 5), and the like where V is deoxyadenylate ("dA"), deoxyguanylate ("dG"), or deoxycytidylate ("dC"). The mixture may contain the primers, such as in Seq. ID. No. 1 through 5, in any ratio.

In some embodiments, the mixture may contain primers having 1, 2, or 3 nucleotides near the 3'-end that can hybridize to an mRNA sequence that is immediately upstream of the polyA tail. Thus, the mixture may contain, in addition to primers of Seq. ID. Nos. 1–5 above, primers having the sequences 5'-TTTTTVVV (Seq. ID. No. 6), 5'-TTTTTVTVV (Seq. ID. No. 7), 5'-TTTTTVVTV (Seq. ID. No. 8), 5'-TTTTTVTVTV (Seq. ID. No. 9), and the like in any ratio. The addition of each nucleotide near the 3'-end will further increase the stability of properly aligned hybrids. In general, the sequence to hybridize to the polyA tail can be decreased by one nucleotide for each additional non-polyA-complementary nucleotide added.

In some embodiments, the mixture may contain primers having more than 3 nucleotides near the 3'-end that can hybridize to the mRNA sequence that is immediately upstream of the polyA tail, including primer having the sequence 5'-TTTTTVVVVV (Seq. ID. No. 10). The 3 or more nucleotides near the 3'-end may be in present in any possible combination, and the mixture may contain the primers in any possible ratio of concentrations. In the most preferred embodiment, the primer mixture contains primers of Seq. ID. No. 2, 3, 4, 5, and 10. The mixture preferably contains Seq. ID. No. 2 at a concentration of about 2% to about 30%, preferably about 10% to about 25%, most preferably about 15% to about 20% of the total concentration of the primers; Seq. ID. No. 3 at a concentration of about 0.5% to about 10%, preferably about 2% to about 8%, most preferably about 3% to about 6% of the total concentration of the primers; Seq. ID. No. 4 at a concentration of about 0.05% to about 10% preferably about 0.1% to about 5%, most preferably about 0.5% to about 3% of the total concentration of the primers; Seq. ID. No. 5 at a concentration of about 0.005% to about 1% preferably about 0.01% to about 0.5% of, most preferably about 0.005% to about 0.05% the total concentration of the primers; and Seq. ID. No. 10 at a concentration of up to about 95%, preferably about 60% to about 80% of the total concentration of the primers. The resultant mixture of primers may be used in a single reaction for the priming of the mRNA for reverse transcription.

In the preferred embodiment, each of the primers in the mixture contains 10 to 20 nucleotides that are capable of hybridizing to the polyA tail, 2 or more nucleotides at one end that can hybridize to the mRNA sequence that is immediately upstream of the polyA tail, and a restriction endonuclease recognition sequence at the other end. Preferably, the restriction enzyme sequence is the same for all the primers in the mixture, and is double stranded. The endonuclease recognition sequence can be any, as is known in the art, and may include BpaI.

The polynucleotide primers may be prepared using any suitable method, such as, for example, the phosphotriester and phosphodiester methods, or automated embodiments thereof. In one such automated embodiment diethylphosphoramidites are used as starting materials and may be synthesized as described by Beaucage et al. (1981) *Tetrahedron Letters* 22: 1859. One method for synthesizing oligonucleotides on a modified solid support is described in U.S. Pat. No. 4,458,066. It is also possible to use a primer which has been isolated from a biological source, such as a restriction endonuclease digest or the like. Methods for preparing and using probes and primers are described in the references, for example Sambrook et al., 1989, *Molecular Cloning: A Laboratory Manual*, $2^{nd}$ ed., vol. 1–3, Cold Spring Harbor Press, Plainview N.Y.; Ausubel et al., 1987, *Current Protocols in Molecular Biology*, Greene Publ. Assoc. & Wiley-Intersciences, New York N.Y.; Innis et al., 1990, *PCR Protocols. A Guide to Methods and Applications*, Academic Press, San Diego Calif. PCR primer pairs can be derived from a known sequence, for example, by using computer programs intended for that purpose such as Primer (Version 0.5, 1991, Whitehead Institute for Biomedical Research, Cambridge Mass.).

The mixture of primers may consist of both the sense and the antisense complement. The sense and antisense mixture of primers may be selected as described in more detail above, and may be present in any stoichiometry, but are generally present in approximately equimolar concentrations in the reaction fluid. Thus, double stranded mixture of primers may be used. In addition, the sense and antisense sequences can be covalently attached using a variety of methods. In one method, the two strands can be linked as a hairpin. Additionally, the strands can be synthesized as a double hairpin and/or ligated to form a closed dumbell (Annu. Rev. Biophys, Biomol. Struct., 25, 1–28, (1996)). Other methods include covalently coupling the sense and antisense strands using standard chemical approaches. One such method of coupling incorporates linker-arms in the complementary strand, where the linker-arm is modified to react primarily with a functional moiety.

The use of the mixture of primers described in more detail above allows for the synthesis of cDNA to begin accurately at the start of the polyA tail of the gene, even in instances where the polyA tail is imperfect in that it may contain non-A nucleotides. The art method of preparing cDNA from mRNA usually result in about 60% successful reads when sequencing from the 3' (polyA tail) end is attempted. In contrast, the use of the mixture of primers of the present invention results in greater than 80% successful reads.

The cDNA prepared by the use of the mixture of primers described in more detail above, may be subsequently modified where the stretch of cDNA corresponding to the mRNA poly-A tail is substantially removed. The removal of the dT stretch of cDNA can be by any means, such as chemical means, enzymatic means, or other means known in the art, and the entire polyT tail may be removed, or a substantial portion of it may be removed. In the preferred embodiment, the restriction endonuclease recognition sequence is used to remove the dT stretch upstream of the site, wherein at least 70% of the dT nucleotides are removed.

The modified cDNA can then be amplified by adding a second known primer, by adding a random primer, or by inserting it unidirectionally into a cloning vector. Oligonucleotides for use as primers may be selected using software known in the art for such purpose. For example, OLIGO 4.06 software is useful for the selection of PCR primer pairs of up to 100 nucleotides each, and for the analysis of oligonucleotides and larger polynucleotides of up to 5,000 nucleotides from an input polynucleotide sequence of up to 32 kilobases. Similar primer selection programs have incorporated additional features for expanded capabilities. For example, the PrimOU primer selection program (available to the public from the Genome Center at University of Texas South West Medical Center, Dallas Tex.) is capable of choosing specific primers from megabase sequences and is thus useful for designing primers on a genome-wide scope. The Primer3 primer selection program (available to the public from the Whitehead Institute/MIT Center for Genome Research, Cambridge Mass.) allows the user to input a "mispriming library," in which sequences to avoid as primer binding sites are user-specified. Primer3 is useful, in particular, for the selection of oligonucleotides for microarrays. (The source code for the latter two primer selection programs may also be obtained from their respective sources and modified to meet the user's specific needs.) The PrimeGen program (available to the public from the UK Human Genome Mapping Project Resource Centre, Cambridge UK) designs primers based on multiple sequence alignments, thereby allowing selection of primers that hybridize to either the most conserved or least conserved regions of aligned nucleic acid sequences. Hence, this program is useful for identification of both unique and conserved oligonucleotides and polynucleotide fragments. The oligonucleotides and polynucleotide fragments identified by any of the above selection methods are useful in hybridization technologies, for example, as PCR or sequencing primers, microarray elements, or specific probes to identify fully or partially complementary polynucleotides in a sample of nucleic acids Methods of oligonucleotide selection are not limited to those described above.

In the preferred embodiment, the modified cDNA sequence is inserted into a cloning vector uni-directionally by methods known in the art. Gubler, U and Hoffman, B. J. (1983) "A simple and very efficient method for generating cDNA libraries" *Gene* 25:263.; Coleclough, C. and Erlitz.F. (1985) "Use of primer restriction end adaptors in a novel cDNA cloning strategy" *Gene.* 34:305. The cDNA libraries may be constructed with the UNIZAP vector system (Stratagene) or SUPERSCRIPT plasmid system (Life Technologies), using the recommended procedures or similar methods known in the art. For most libraries, the cDNA may be size-selected (300–1000 bp) using SEPHACRYL S1000, SEPHAROSE CL2B, or SEPHAROSE CL4B column chromatography (Amersham Pharmacia Biotech) or preparative agarose gel electrophoresis. cDNAs may be ligated into compatible restriction enzyme sites of the polylinker of a suitable plasmid, e.g., PBLUESCRIPT plasmid (Stratagene), PSPORT1 plasmid (Life Technologies), PCDNA2.1 plasmid (Invitrogen, Carlsbad Calif.), or pINCY (Incyte Pharmaceuticals, Palo Alto Calif.). Recombinant plasmids may be transformed into competent *E. coli* cells including XL1-Blue, XL1-BlueMRF, or SOLR from Stratagene or DH5α, DH10B, or ElectroMAX DH10B from Life Technologies.

The cDNA libraries can be used to determine quantitative information about the genetic profile of the nucleic acids in the sample that was contacted with the array to generate the hybridization pattern, as well as the physiological source from which the labeled sample nucleic acid was derived. The data provides information about the physiological source from which the sample nucleic acid were derived, such as the types of genes expressed in the tissue or cell which is the physiological source, as well as the levels of expression of each gene, particularly in quantitative terms.

The present method can be used in comparing nucleic acid samples from two or more physiological sources to identify and quantify differences between the patterns thereby providing data on the differential expression of a particular gene in the physiological sources being compared. Thus the methods of the invention find use in differential gene expression assays for the analysis of a diseased and normal tissue, analysis of a different tissue or subtissue types, and the like. Thus, this data may be used for large scale correlation studies on the sequences, mutations, variants, or polymorphisms among samples.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperatures, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

This example serves to demonstrate a method of making the mixture of primers for use in the invention.

The primers having the sequences of Seq I.D. No. 11 through 16 (below), also shown in FIG. 1, were made by synthetic methods.

```
5'pGACTAGTTCTAGATCGCGACTGGATTTTTTTTTTTTTTTTVV      Seq ID. No.11

5'pGACTAGTTCTAGATCGCGACTGGATTTTTTTTTTTTTTTTVTV     Seq ID. No.12

5'pGACTAGTTCTAGATCGCGACTGGATTTTTTTTTTTTTTTVTTV     Seq ID. No.13

5'pGACTAGTTCTAGATCGCGACTGGATTTTTTTTTTTTTTVTTTV     Seq ID. No.14

5'pGACTAGTTCTAGATCGCGACTGGATTTTTTTTTTTTTTVVVVV     Seq ID. No.15
```

The primer mixture made by mixing together about 18.85% of the double stranded primer having Seq I.D. No. 11, about 4.69% of the double stranded primer having Seq I.D. No. 12, about 1.17% of the double stranded primer having Seq I.D. No. 13, about 0.029% of the double stranded primer having Seq I.D. No. 14, and about 75.0% of the double stranded primer having Seq I.D. No. 15.

Example 2

This example serves to demonstrate a method for the synthesis of the first strand.

mRNA was synthesized or isolated from tissue samples. The tissue samples were homogenized and lysed in guanidinium isothiocyanate, or they were homogenized and lysed in phenol or in a suitable mixture of denaturants, such as TRIZOL (Life Technologies), a monophasic solution of phenol and guanidine isothiocyanate. The resulting lysates were centrifuged over CsCl cushions or extracted with chloroform. RNA was precipitated from the lysates with either isopropanol or sodium acetate and ethanol, or by other routine methods.

Phenol extraction and precipitation of RNA were repeated as necessary to increase RNA purity. In some cases, RNA was treated with DNase. For most libraries, poly(A+) RNA was isolated using oligo d(T)-coupled paramagnetic particles (Promega), OLIGOTEX latex particles (QIAGEN, Chatsworth Calif.), or an OLIGOTEX mRNA purification kit (QIAGEN). Alternatively, RNA was isolated directly from tissue lysates using other RNA isolation kits, e.g., the POLY(A)PURE mRNA purification kit (Ambion, Austin Tex.).

The mRNA (1.5 µg) was resuspended in 10 µl of DEPC treated water, denatured by heating the RNA to about 70° C. for 10 min., and then quick-chilled on ice. Reverse transcription was initiated using the primer mixture of Example 1 (0.5 µg in 1 µl of water), heating the mixture to about 70° C. for 10 min., and then quick-chill on ice. The mixture was briefly centrifuged, and the solid contents at the bottom of the tube were collected. The contents were then cooled on ice, and 4 ml 5×first strand buffer, 2 ml 0.1 M DTT, 1 ml 10 mM dNTP (with methyl dCTP) mix, and 1 ml a-[$^{32}$P]dCTP (10 uCi/ul) were added and the contents were mixed by gently vortexing. The reaction mixture was briefly centrifuged and the solid contents at the bottom were collected. To the solid contents were added 1 µl of deletion mut_MML V-RT (200 µ/µl) from Promega or Superscript I, and the total reaction volume was about 20 µl. Other reverse transcriptases, point mutations or native should not be substituted. The reaction mixture was gently mixed and incubated at about 37° C. for approximately 1 h. and then incubated at 70° C. for approximately 10 min., followed by quick chill on ice.

Example 3

This example serves to demonstrate a method for the synthesis of the second strand.

The reaction tube from Example 2, containing the first strand was placed on ice, and 92 µl of DEPC-treated water, 30 µl of 5×second strand buffer, 3 µl of 10 mM dNTP mixture, 1 µl 100 mM dCTP, 1 µl of *E. coli* ligase (10 U/µl), 4 µl of *E. coli* DNA polymerase I(10 U/µl), and 1 µl of *E.coli* RnaseH (2 U/µl) were added. The reaction mixture was gently mixed, incubated at 16° C. for 2 h, followed by the addition of 2 µl of DNA polymerase with further incubation at 16° C. for 5 min. The sample was then partitioned into approximately two equal parts and each was size selected using a Chromospin CR-1000 column (Clontech). Next, an equal volume of phenol:chloroform:isoamyl alcohol (25:24:1) was added, and the reaction mixture was stirred by vortexing, and the two phases were separated by centrifugation at room temperature for 5 min. at 14,000×g. The aqueous layer was removed and transferred to a new tube. To the aqueous layer were added about ½ volume of 7.5 M NH$_4$OAc, 1 µl of glycogen (20 µg) followed by 2.5 volumes of 100% ethanol. The reaction mixture was stirred by vortexing followed by centrifugation at 14,000×g for 15 min. at room temperature. The supernatant was carefully removed, and the pellet rinsed twice with 200 µl of cold 70% ethanol by centrifugation at 14,000×g for 2 min. The ethanol was removed, and the pellet was resuspended in 34 µl of water, and 10 µl of 5×T4 ligase buffer, 1 µl of EcoR1-XhoI adapters (1 µg/µl; Stratagene) and 5 µl of T4 DNA ligase were added. The final volume of the reactants was about 50 µl. The mixture was gently mixed and incubated overnight at 16° C. The next day, the about 150 µl of DEPC water was added, and an equal volume of phenol:chloroform:isoamyl alcohol (25:24:1) was added, and the reaction mixture was stirred by vortexing, and the two phases were separated by centrifugation at room temperature for 5 min. at 14,000×g. The aqueous layer was removed and transferred to a new 1.5 ml tube. To the aqueous layer were added about ½ volume of 7.5 M NH$_4$OAc, 1 µl of glycogen (20 µg) followed by 2.5 volumes of 100% ethanol. The reaction mixture was stirred by vortexing followed by centrifugation at 14,000×g for 15 min. at room temperature. The supernatant was carefully removed, and the pellet rinsed twice with 200 µl of cold 70% ethanol by centrifugation at 14,000×g for 2 min. The ethanol was removed by air drying the pellet for 5–10 min, and the pellet was resuspended in 40.5 µl of DEPC water for digestion with Bpm I restriction enzyme (NEB).

Example 4

This example serves to demonstrate the method used to shorten the polyA tail-primer complement in the cDNA to generate a 3'-A-A overhang.

To the solution from Example 3 were added 5 µl of 10×buffer 3, 0.5 µl of 100×BSA and 4 µl of Bpm I (NEB). The mixture was mixed gently, and incubated for at least 4–5 h at 37° C. Then 150 µl of DEPC water was added, and an equal volume of phenol:chloroform:isoamyl alcohol (25:24:1) was added, and the reaction mixture was stirred by vortexing, and the two phases were separated by centrifugation at room temperature for 5 min. at 14,000×g. The aqueous layer was removed and transferred to a new 1.5 ml tube. To the aqueous layer were added about ½ volume of 7.5 M NH$_4$OAc, 3.5 µl of yeast tRNA (1 µg/µl) followed by 2.5 volumes of 100% ethanol. The reaction mixture was stirred by vortexing followed by centrifugation at 14,000×g for 15 min. at room temperature. The supernatant was carefully removed, and the pellet rinsed twice with 200 µl of cold 70% ethanol by centrifugation at 14,000×g for 2 min. The pellet was air dried bor 5–10 min, and re-suspended in 70 µl of STE.

Example 5

This example serves to demonstrate the ligation of cDNA into KS+/BsgI

The cDNA of Example 4 was size selected using a sepharose column. The vector was prepared by known methods by cutting sequentially with BsgI overnight, then with EcoRI and finally with BamHI. The cut vector was purified by gel chromatography.

Into a 1.5 ml micro-centrifuge tube were placed 2 µl 5×DNA ligase buffer, 1 µl (25 ng/µl) of the cut vector, 10 ng of the purified cDNA, and water to a total volume of 9 µl. To the mixture was then added 1 µl of T4 DNA ligase. The reaction mixture was mixed by gently vortexing, and the contents were quick-spun to the bottom of the tube, and incubated at room temperature for 2 h, or overnight at 16° C.

Example 6

This example presents the results from DNA sequencing.

Out of the 576 clones that were attempted in cycle sequencing for three rat libraries, usable sequences were obtained from 503 clones (87.3% success rate). The average usable length was 588 base pairs with an average of 563 bases with Phred 20 or higher. There was only trace to non-detectable levels of contamination with ribosomal, mitochondrial or clones with poly A/T stretches. When a comparison against Rat EST database was performed, a very high confirmation rate was obtained between the sequences using the method of the present method and ESTs produced by the TN-wobble primer based sequencing. In total 269 pairs of sequences were analyzed. A significant number of clones produced 3' extensions to our database, and only 8 clones were more than 50 base pairs 5' of the database entry.

What is claimed is:

1. A method for obtaining a DNA complementary to a mRNA, the method comprising:
   contacting the mRNA having a polyadenosine (polyA) tail with a primer mixture, the mixture comprising a plurality of primers wherein each primer comprises at least 5 contiguous deoxythymidines at a 3' end of the primer, and at least 2 independently selected non-deoxythymidine nucleotides positioned 3' of the contiguous deoxythymidine nucleotides, wherein the non-deoxythymidine nucleotides comprise a sequence selected from the group consisting of VV, VTV, VTVV, VTVVV, VTVVTV, VTTV, VTTTV, VTVVV, and VVVVV and combinations thereof, wherein V is deoxyadenosine, deoxycytidine, or deoxyguanosine; and
   reverse transcribing the mRNA using a reverse transcriptase to produce a DNA strand complementary to the mRNA.

2. The method of claim 1, wherein each primer further comprises a restriction enzyme sequence near the end opposite to the one containing the non-deoxythymidine nucleotides.

3. The method of claim 2, wherein the restriction enzyme sequence is double stranded.

4. The method of claim 1, wherein each primer comprises at least 10 contiguous deoxythymidines.

5. The method of claim 1, wherein each primer comprises at least 15 contiguous deoxythymidines.

6. The method of claim 1, wherein the mixture comprises about 10–25% of a primer having a VV, about 0.5–10% of a primer having a VTV, about 0.1–5% of a primer having a VTTV, about 0.001–0.5% of a primer having a VTTTV, and up to about 95% of a primer having a VVVVV, wherein V is deoxyadenosine, deoxycytidine, or deoxyguanosine.

7. The method of claim 6, wherein the mixture comprises about 15–2% of a primer having a VV, about 3–6% of a primer having a VTV, about 0.5–3% of a primer having a VTTV, about 0.005–0.05% of a primer having a VTTTV, and about 60–80% of a primer having a VVVVV, wherein V is deoxyadenosine, deoxycytidine, or deoxyguanosine.

8. A method for obtaining a DNA complementary to a mRNA, the method comprising:

contacting the mRNA having a polyA tail with a primer mixture comprising a plurality of primers wherein each primer comprises at least 10 contiguous deoxythymidines and a non-polyA-complementary region near one end, wherein the non-polyA-complementary region is selected from the group consisting of VV, VTV, VTVV, VTVVV, VTVVTV, VTTV, VTTTV, VVTVVV, and VVVVV, and combinations thereof, wherein V is deoxyadenosine, deoxycytidine, or deoxyguanosine; and reverse transcribing the mRNA using a reverse transcriptase to produce a DNA strand complementary to the mRNA.

9. The method of claim 8, wherein the restriction enzyme sequence is double stranded.

10. The method of claim 8, wherein each primer comprises at least 15 contiguous deoxythymidines.

11. The method of claim 8, wherein the mixture comprises about 10–25% of a primer having a VV, about 0.5–10% of a primer having a VTV, about 0.1–5% of a primer having a VTTV, about 0.001–0.5% of a primer having a VTTTV, and up to about 95% of a primer having a VVVVV, wherein V is deoxyadenosine, deoxycytidine, or deoxyguanosine.

12. The method of claim 8, wherein the mixture comprises about 15–20% of a primer having a VV, about 3–6% of a primer having a VTV, about 0.5–3% of a primer having a VTTV, about 0.005–0.05% of a primer having a VTTTV, and about 60–80% of a primer having a VVVVV, wherein V is deoxyadenosine, deoxycyridine, or deoxyguanosine.

\* \* \* \* \*